(12) United States Patent
Zlochin

(10) Patent No.: US 6,575,621 B1
(45) Date of Patent: Jun. 10, 2003

(54) DEW POINT HYGROMETERS AND DEW SENSORS

(75) Inventor: Igor Zlochin, Haifa (IL)

(73) Assignee: Optiguide Ltd., Yokneam Illit (IL)

(*) Notice: Subject to any disclaimer, the term of this patent is extended or adjusted under 35 U.S.C. 154(b) by 0 days.

(21) Appl. No.: 09/830,494
(22) PCT Filed: Oct. 29, 1999
(86) PCT No.: PCT/IL99/00571
§ 371 (c)(1), (2), (4) Date: Jul. 13, 2001
(87) PCT Pub. No.: WO00/26652
PCT Pub. Date: May 11, 2000

(30) Foreign Application Priority Data

Oct. 30, 1998 (IL) ............................................... 126826

(51) Int. Cl.⁷ .......................... G01N 25/02; G01R 27/26
(52) U.S. Cl. ............................ 374/28; 374/16; 374/21; 324/658; 324/661; 324/664; 73/335.04; 73/170.17
(58) Field of Search .................. 374/16, 17, 18, 374/19, 20, 21, 28; 73/170.17, 170.18, 170.19, 170.21, 170.22, 170.23, 335.04; 324/664, 658, 661

(56) References Cited

U.S. PATENT DOCUMENTS

| | | | |
|---|---|---|---|
| 3,611,788 A | | 10/1971 | Amelkin et al. ............ 73/17 A |
| 3,623,356 A | | 11/1971 | Bisberg ....................... 73/17 A |
| 4,216,669 A | | 8/1980 | Harding, Jr. ................ 73/17 A |
| 4,626,774 A | | 12/1986 | Regtien ...................... 324/61 R |
| 4,877,329 A | * | 10/1989 | Sauerbaum et al. .......... 374/28 |
| 4,898,476 A | * | 2/1990 | Herrmann et al. ............. 374/28 |
| 4,948,263 A | | 8/1990 | Herrmann et al. ............. 374/28 |
| 5,024,532 A | * | 6/1991 | Rall ............................. 374/28 |
| 5,028,906 A | * | 7/1991 | Moriya et al. ................ 338/35 |
| 5,345,821 A | * | 9/1994 | Reich et al. ............... 73/335.04 |
| 5,364,185 A | * | 11/1994 | VanZandt et al. ............ 374/28 |
| 5,402,075 A | | 3/1995 | Lu et al. ..................... 324/664 |
| 5,533,393 A | * | 7/1996 | Bonne et al. ............. 73/335.02 |
| 5,726,622 A | * | 3/1998 | Furuyama et al. ............ 338/35 |
| 6,022,138 A | * | 2/2000 | Sonander ..................... 374/28 |
| 6,126,311 A | * | 10/2000 | Schuh ......................... 374/21 |

FOREIGN PATENT DOCUMENTS

| | | | | |
|---|---|---|---|---|
| DE | 3713864 | | 11/1988 | |
| DE | 3843341 | | 6/1990 | |
| DE | 4423179 | | 1/1996 | |
| GB | 2078973 A | * | 1/1982 | ......... G01N/27/22 |
| GB | 2298042 | | 8/1996 | |
| JP | 61018850 A | * | 1/1986 | ......... G01N/27/22 |
| JP | 06194114 A | * | 7/1994 | ......... G01B/07/06 |
| JP | 2000-114090 A | * | 4/2000 | ......... H01G/04/06 |
| WO | 9201927 | | 2/1992 | |
| WO | 9219954 | | 11/1992 | |
| WO | 9605506 | | 2/1996 | |

OTHER PUBLICATIONS

English Abstract of DE 371 3864 dated Nov. 17, 1988.
English Abstract of DE 384 3341 dated Jun. 28, 1990.
Derwent Abstract of DE 442 3179 dated Jan. 4, 1996.
Matsumoto, S. et al. "Determination of the dew point using laser light and a rough surface".
Optics Communications, vol. 91, No. 1/2, p. 5–8, (1992).
Jachowicz, R.S. et al. "Hygrometer with fibre optic dew point detector" Sensors and Actuators A, vol. 41–42, p. 503–507, (1994).
Wiederhold, P. R. "The Cycling Chilled Mirror Dew Point Hygrometer" Sensors, p. 25–27, Jul. 1996.

* cited by examiner

*Primary Examiner*—Diego F. F. Gutierrez
*Assistant Examiner*—Lydia M. De Jesús
(74) *Attorney, Agent, or Firm*—Ladas & Parry

(57) ABSTRACT

The invention concerns dew point hygrometers based on condensation of dew on ends of optical fibers, or on surfaces of an optical prism. The invention also concerns a dew sensor for determining the natural dew condensation by optical means and a dew sensor capable of detecting dew by detecting a change in capacitance.

4 Claims, 5 Drawing Sheets

DEW POINT HYGROMETERS AND DEW SENSORS

FIELD OF THE INVENTION

The present invention concerns dew point hygrometers for determining the dew point of gas and dew sensors for determining the neutral dew condensation. More specifically the present invention concerns hygrometers comprising optic fibers, or hygrometers based on change of capacitance.

BACKGROUND OF THE INVENTION

State of the art hygrometers used in agriculture, notably in greenhouses, operate by usually falling into one of the following three types. The first is a psychrometer which requires a very high degree of maintenance. The second is a relative humidity meter which principle of operation is based on the change of capacity, which is very problematic when determining relatively high humidity. Cheap instruments based on capacitance measuring are unreliable since the reading changes in time independently of changes in the humidity content of the air. The third type of sensors are dew point hygrometers based on optic mirrors, which are very expensive, and unsuitable for routine work at greenhouse conditions since the require constant cleaning of the mirror's surface.

In the past decade, with the availability of thermoelectric coolers and solid state instrumentations the optical condensation type dew point hygrometer has become one of the most accurate and reliable humidity instruments, offering broad dew point range and excellent repeatability.

In the optical dew point hygrometer, a condensation surface which is usually a mirror is cooled by a thermoelectric or Peltier cooler until dew or frost begins to condense on the mirror. The condensation surface is maintained in vapor pressure equilibrium with the surrounding gas, and the amount of condensation on the surface is detected by optical techniques. The temperature of the condensation surface at which the rate of the condensate exactly equals the evaporation, is defined as the dew point temperature. The temperature of the surface when so controlled is typically measured with a platinum resistance thermometer, a thermocouple or thermistor embedded in the mirror surface.

This condensation-type dew point hygrometer is suitable for applications in which a maximum accuracy of the water vapor content is needed over a fairly wide range of dew points, and is suitable for applications in which there is a chance of routine contamination with oils, corrosive gases, salts or similar contaminants that are known permanently damage other types of hygrosensors. Typically, optical dew points are used in industries where precise determination of water vapor in the gas is necessary, such as in pharmaceutical manufacture, electronic, chemical and gas/oil refinery industries, meteorology and food industries, in greenhouses and the like.

One of the main drawbacks of optical condensation-type dew point hygrometers is contamination by materials other than the water condensing on the cooled surface, for example, contamination by various salt solutes. This contamination generally reduces the accuracy of the dew point measurement to a degree which depends on the amount of the contaminant present and its solubility in water. Both soluble and insoluble materials, if allowed to build up on the condensing surface, will eventually cause the system to go out of control because of reduced mirror reflectance. In prior art systems, heating of the mirror to the dry state for manual or automatic rebalancing of the optical detection circuit, overcomes the loop offset problem associated with reduced reflectance, but does not address the problem of measurement error associated with vapor pressure modification as induced by soluble mater. The soluble materials such as salts precipitate out and form a thin layer on the mirror surface. The salts tend to absorb water vapor at temperatures above the dew point and dissolve back into dew layer when the mirror recools. The temperature of the contaminated mirror therefore does not reach the true dew point even after compensating for the reduced reflectance. The resultant dew layer contains salts which cause the saturation vapor pressure to decrease.

Several patents were designed to address this problem. U.S. Pat. No. 3,623,356 is directed to a dew point hygrometer in which there is manual or automatic disabling of the feedback control system which controls the temperature of the mirror, thus forcing the mirror surface to heat to a dry state at which time an additional current is injected into the control loop amplifier at the photodetector bridge circuit. The bridge circuit compensates for changes in the reflective characteristics of the mirror due to accumulation of contamination.

U.S. Pat. No. 4,216,669 periodically interrupts control of the condensing temperature, by periodically cooling the condensing surface (i.e. the mirror) to a temperature well below the prevailing dew point for a time sufficient to provide a heavy growth and coalescence of the condensate so as to dissolve all the soluble material and create a medium by which molecules of solute can migrate. Immediately after cooling the condensing surface is heated to a temperature well above the prevailing dew point so as to cause total evaporation of the solvent (condensate) and recrystallization or precipitation of solute into relatively large clusters or isolated colonies. This leaves most of the area of the condensing surface clear or solid deposits and extends the time period required between mirror cleanings by a factor of 10 to 100 times.

Pieter R. Wiederhold in "*The Cycling Chilled Mirror Dew Point Hygrometer*". Sensors, July 1966, pp. 25–27 discusses the cycling chilled mirror (CCM) hygrometer, wherein the mirror temperature is lowered at a precisely controlled rate until dew formation is detected. Before the dew sample can form a continuous layer on the mirror, the mirror is heated and the dew on the mirror surface is evaporated. The mirror is therefore almost always (95% of the time) in the drop state and contains a dew, layer for only 5% of the time, when a dew point is made. The measurement cycle is typically once every 20 s. Because dew is present on the mirror surface for only a very short time, contaminant build-up on the mirror is kept at an absolute minimum. Surrounding the mirror is the cylindrical, 40 micron filter. In contrast to the in-line filters used with conventional hygrometer systems, this filter does not require that 100% of the total sample gas pass through its element. Instead, sample gas circulates around the outside of the element and is measured by means of convection across the filter element. Because most particulates circulate freely around the filter and exit the measurement chamber, the filter is slow to become contaminated. This arrangement has a slow response time and is relatively inaccurate.

For high-temperature applications, a model has been developed that uses fiber-optic bundles that isolate the temperature-sensitive electro-optical components from the high-temperature environment.

Prior art also teaches optical dew point hygrometers in which the ends of optic fibers are used as the condensing surface. Use of optic fibers instead of mirrors features the advantage of high resistance to a wide variety of chemicals and considerably decrease the cost of producing said hygrometers. However, the problems of contaminant, due to build up of solid deposits on the surfaces of the optic fibers, is very similar to that encountered in dew point hygrometers wherein mirrors are the condensing surfaces, and is a major obstacle in providing dew point hygrometers that are accurate and reliable over long periods of time.

Another device for sensing humidity is a dew sensor (as opposed to a dew point hygrometer). This sensor in fact mimics the condensation of humidity on a natural surface such as on leaves, without control of the temperature of the sensor, and thus in fact is very reliable since it directly mimics the natural process of condensation. Various measurements have shown a good correlation between the temperature of the leaf and the temperature of the dew sensor at night. Thus, such a sensor is suitable for use in detecting condensation of water on various surfaces, such as leaves in greenhouses, giving a warning when a humidity of the air is too high, a situation which occurs for example at night, which is a cause of many plant diseases. Such a warning may operate various drying mechanisms in order to lower again Greenhouse humidity.

In fact at night the dew sensor, is more suitable for use than dew point hygrometers in greenhouses, since it indeed reflects the true and natural situation of condensation on surfaces, which is a better predictor to the state of the leaves than humidity content detected by dew point hygrometers.

Conventional dew sensors such as those used in greenhouses typically employ a pair of spaced electrical wires, the resistance between which drops from approximately 19 megohms to 3 megohms when dew bridges the two wires. But such devices are electrically noisy and have changable sensitivity that depends on salts precipitation on the sensor. Another problem with such devices is that generally require high voltage and the explosure of the conductors and leads which features renders them vulnerable to corrosion by the weather. The corrosion is especially rapid in the presence of high voltages used in the range of 1 to 20 volts.

U.S. Pat. No. 4,948.263 is directed, to a dew point sensor for a dew-point measuring device for measuring the water vapor dew point in gases comprising a sensor surface which is exposed to the gas to be measured and on which, upon cooling, the dew-point temperature water vapor condenses. Mounted on the sensor surface are two electrode structures which comprise electrode portions which are arranged a uniform interval parrallel to each other and which are covered with a moisture-insentive insulating layer. The reaching of the dew-point temperature is determined by measuring the impedance or capacitance between the two electrode structures. The distance between the electrode portions, arranged parallel to each other, of the two electrode structures is of the order of magnitude of the diameter of the largest condensation droplet forming on reaching the dew-point temperature, or smaller than said diameter, and the thickness of the insulating layer is small compared with the distance between the electrode portions.

U.S. Pat. No. 4,626,774 is directed to a dew-point measuring instrument which has a capacitive dew-point sensor which is cooled by a cooling device to the dew-point temperature measured by, a temperature sensor. A phase measuring circuit measures the phase angle of the impedance of the capacitive dew-point sensor. The measured phase angle is used as a gauge for the contamination of the dew-point sensor.

U.S. Pat. No. 5.402.075 is directed to a capacitive moisture sensor includes insulator means; capacitance means including a sensing capacitor having a plurality of spaced capacitive sensor conductors mounted with the insulator means for exposure to the atmosphere; and first and second electrodes mounted with the insulator means remote from the spaced capacitive sensor conductors: means for applying a periodic input current across the first and second electrodes; and means for detecting a change in capacitance between the first and second electrodes indicative of moisture bridging at least two of the capacitive sensor conductors.

SUMMARY OF THE INVENTION

Bat a first embodiment termed the "fiber optical dew point hygrometer" the present invention concerns dew point hygrometers for determining dew point of a gas, comprising optic fibers, in which the problem of solid contaminants deposited on the condensing surface is significantly reduced by periodically restoring the end of the optic fiber, which serves as the condensing surface, to its original contamination-free state.

The present invention provides a dew point hygrometer for determining dew point of a gas, comprising:
a light emitter and a light detector optically coupled through a light path defined by at least one optic fiber, the path comprising at least one sensing gap, said gap is formed between the ends of two optic fibers, between the end of an optic fiber and the light emitter or between the end of an optic fiber and the light detector; at least one end of an optic fiber forming the sensing gap is a dew forming end in contact with said gas, on which dew can form, changing light transmitted through the gap to the light detector:

temperature control devices for controlling temperature of the dew forming end and the air adjacent to said dew forming end:

restoration means for essentially restoring original light transmittance through the dew forming end, which can otherwise be impaired by solid deposits thereon during operation, and control mechanism for controlling operation of said temperature control devices and for automatic activation of said restoration means after an operation phase of the hygrometer.

The gas which vapor contact or dew point is to be determined may be any type of gas typically air, or $N_2O$, $CO_2$, $O_2$ and monitoring of dryness of inert gases.

By a second embodiment termed the "fiber optical dew sensor embodiment" the present invention concerns a sensor for determining the natural dew condensations, i.e. the dew condensation on surfaces such as leaves in greenhouses. This sensor s temperature changes freely with the change of ambient temperature, humidity and cooling by radiation and is not controlled, thus truly reflecting the natural state of dew.

By this embodiment the present invention concerns a dew sensor for determining the natural dew condensation on a surface comprising:
a light emitter and a light detector optically coupled through a light path defined by at least one optic fiber, the path comprising at least one sensing gap which is formed between the two ends of two optic fibers or between the end of an optic fiber and the light detector; at least one end of an optic fiber forming the sensing gap is a dew forming end in contact with said air, on which the dew can form, chancing light transmitted from the light emitter through the gap to the light detector;

the optic fibers being embedded into a plate, having a temperature essentially similar to that of the surface: and control mechanism for monitoring of said light path condition, elimination of sun radiation and contamination influence and controlling of said light emitter and detector operation.

The plate's temperature mimics as close as possible the temperature of the leaf at night For example, when used in greenhouses it is cooled by infrared emission directed from the plate to a cooler region, for example, during the night from the plate to the cool sky. An example of such a plate is PVC plate.

According to said second embodiment, it is preferable that the deal forming ends are rough, in order to speed the dew condensation onset. In addition, said rough ends, increase the sensitivity of the sensor, since accumulation of liquid, serves to "smooth " said rough ends, thus increasing the difference between the dry and wet conditions.

The dew sensitivity of the sensor may be changed by varying the roughness of the dew forming end, for example by replacing said end with another end having a different degree of roughness.

In addition, in accordance with the second embodiment, it is preferable that the sensor also comprises means for protecting the light path from contamination, such as various sieves, filters, protection tubes, surrounding the light path and avoiding penetration of contaminants to the light path.

The dew sensitivity of the sensors may be changed by changing one or more of the following parameters:

optic fiber diameters;

gap size;

change of post-period to post duration ratio of the light transmitter, so that the light transmitted through the zap heats the dew forming end an, evaporates the dew condensed on the end:

the dew sensitivity and contamination protection value of the sensor may be changed by the change of the means for protecting from contamination, for example where the protecting means is a tube having a filter at its end by the change in protecting the tube's length;

the dew sensitivity of the sensor may be changed by cooling the plate with a thermoelectric cooler;

the dew sensitivity of the sensor may be also changed by changing the infrared emission and the heat conduction range of the plate in which the optic fibers are embedded, for example by changing the material, color or roughness of the plate.

The control mechanism of the second embodiment subtracts sun radiation signal from the total signal on the light detector (which reaches both light emitted from the light transmitter plus sun radiation signal), interrupts the dew onset monitoring at day according to the light transmitter and sun radiation ratio, measures the optical transmittance when the sensor is at dry state, and calibrates the sensor's threshold sensitivity according to "dry ends light transmittance".

The dew which the sensor detects is usually water condensation. By a preferable option the dew sensor may also comprise restoring means as will be explained hereinbelow.

Light emitters according to optical embodiments are any means capable of emitting visible or infrared light, for example, HFBR-2524 Hewlett Packard Transmitter (Hewlett Packard. Components, USA).

The light detector according to optical embodiments is a device capable of receiving light and transducing the light received to an easily detectable signal such as electrical currents, which may be digitally represented. Examples of light detectors are HFBR-1524 receiver (Hewlett Packard Components, USA).

The light emitter and light detector are coupled through a light path defined by at least one optic fiber. The path comprises at least one sensing gap which is in contact with the gas (in case of hygrometer) or air (in case of dew sensor). When the hygrometer or the dew sensor is composed of a single optic fiber the sensing gap may be between the fiber and the light emitter (when the fiber is attached to the light detector); the fiber and the light detector (when the fiber is attached to the light emitter); or the hygrometer or dew sensor may comprise at least two gaps, one between the optic fiber and the light emitter and the other between the optic fiber and the light detector (when the optic fiber is spaced both from the light emitter and the light detector).

The gap(s) may also be formed between ends of two or more optic fibers, for example where the hygrometer or dew sensor comprises two optic fibers a single gap may be formed between a first optic fiber attached to the light emitter and a second optic fiber attached to the light detector. Alternatively, when the hygrometer or dew sensor comprises two optic fibers two gaps may be formed: one between a first optic fiber (attached to the light emitter) and a second unattached optic fiber, and the other between the unattached optic fiber and the light detector.

The hygrometer or dew sensor of the invention may also comprise three optic fibers: one coupled to the light emitter (a first peripheral optic fiber) one coupled to the light detector (a second peripheral optic fiber) and one present in between the two and spaced therefrom (an intermediate optic fiber) so as to form at least two sensing gaps, between the end intermediate optic fiber and each of the uncoupled end peripheral optic fibers.

Each sensing gap is formed by at least one end of the optic fiber, on which dew can form. This end is termed "the dew forming end". Formation of dew on said end changes the light transmitted from the light emitter through the gap to the light detector. Where the surfaces of the dew forming ends are smooth, i.e. polished, formation of dew thereon decreases the light transmitted through the gap. Where the surfaces of the dew forming ends are rough (grinded) dew formed thereon increases light transmittance.

In connection with the first embodiment "the dew point hygrometer" the temperature control device comprises a heating/cooling means such as a thermoelectric cooler, for example, SP1652. Harlox Industries Inc. (USA) thermoelectric cooler can control the temperature of the dew forming end.

The control mechanism of the dew point hygrometer is typically capable of controlling the temperature control device by a servo mechanism. In addition the control mechanism can activate the restoration means automatically, either by activating it periodically, for example, utilizing a timer, or activating it after a certain amount of contamination has build up on the dew forming end, which build up is detected by decrease of the optical transmittance when the hygrometer is at a dry state. Both types of activation (after specific time periods or after a certain amount of contamination has built up) are termed "an operation phase".

The detection of the dew in gas can be determined by maintaining the temperature of the dew forming end in vapor pressure equilibrium with the surrounding gas, i.e. the dew forming end is maintained at the temperature at which the rate of condensate exactly equals the evaporation, and this temperature is then defined as the dew point temperature and correlates exactly to the dew contents of the gas.

The restoring means, are intended to restore the dew forming end(s) to its/their original form. i.e. without the contamination of various solid deposits thereon, so as to restore original light transmittance through the dew forming end.

According to a first option of the invention suitable mostly for the dew point hygrometer embodiment, the restoring means comprise a gas blower, capable of blowing gas on the dew forming end. According to this embodiment, the temperature control device, periodically cools the dew forming ends of the optic fiber to a temperature well below the dew forming temperature, so that a heavy growth and coalescence of the condensate is formed, thereby dissolving all of the soluble material deposited on the optic fiber ends or loosening non-soluble material. Immediately after said cooling, the air blower blows an air stream strong enough to blow away the condensate together with the solid deposits contained or dissolved therein, and thus the dew forming ends of the optic fiber are cleared. The cooling, of the end forming end and the blowing of the gas are controlled and timed by the controlling mechanism.

According to a second option of the invention, the restoring means comprise a displaceable transparent film covering the end of the optic fiber, so that said displaceable film actually constitutes the condensing surface. The dew forms on a portion of the film instead of directly on the end of the optic fiber. Periodically, the film is displaced, so that another clean portion of the film comes into contact with the end of the optic fiber, said end being clear of deposited contaminants. The film may be for example a transparent band made of Polyester™ (Lee Filters (U.K.)) linearly displaceable over the end of the optic fiber.

According to a third option of the invention, the restoring means are capable of periodically breaking a small segment of the optic fiber at the dew forming end, and thus exposing a new, uncontaminated dew forming end. Said restoring means, may be for example in the form of a cutting knife, capable of slicing a small section of the optic fiber containing contaminants deposited thereon, and exposing a new and clean end.

According to a fourth option of the invention, at least one of the optic fibers, which form the sensing gap, is a member of a plurality of optic fibers, for example, arranged in a battery. Periodically, the previously used optic fiber is replaced by a new optic fiber from the batter), which is clean and has no deposits of contaminants on its end.

By a third embodiment of the invention. called "condensation film embodiment" a condensation film, for example made of transparent synthetic film, is placed on a thermoelectric cooler to increase the sensitivity of the dew point hygrometer or dew sensor. While cooling the condensation film, vapor, such as water vapor condenses on the film. Two optic fibers are placed in an angle in respect to the film. one connected to a light emitter and one to a light detector measuring the light reflected from the film. Condensation of liquid on external side of the film (i.e. the side not in contact with the thermoelectric cooler) leads to change in the reflected light from both sides of the film. The temperature of the film and the air is measured and the result is calibrated to give the amount of humidity in the air. Periodically the film is mobilized. so that each period of time (for example each couple of days) a new and clean portion of the film is available for condensation and measurement of reflector thereon. 23. In a preferred embodiment of the dew point hygrometer, operating under a stable temperature condition as, for example. in a refrigerator, the temperature control device is a thermoelectrical cooler capable of measuring the relative humidity of the air by measuring the current of the thermoelectrical cooler in the course of dew condensation on the film.

By a fourth embodiment of the invention called "condensation prism embodiment" an optical prism is placed on a thermoelectric cooler to increase the sensitivity of the dew point hygrometer. A light emitter and a light detector optically coupled through a light path defined by a least two surfaces of the prism. The humidity condenses on the surfaces of said prism, thus changing the amount of light sensed by the light detector. The thermoelectric cooler's temperature can be controlled by control mechanism. which when determining the temperature at which condensation begins to form can deform the dew point.

By a fifth embodiment of the invention termed the "capacitive dew sensor embodiment" the present invention concerns a capacitive dew sensor, in which the problem of solid contaminants (salts, dust and so on) deposited on the outside surface of the sensor and electrode's corrosion are significantly reduced by using a water layer as a one of the capacitor's electrodes.

The sensor includes two electrode structures separated from each other by an insulator and wires, connecting each of the electrodes to a measuring circuit. The first electrode structure is a conductive plate mounted on one surface of the insulator. The first electrode is isolated from the ambient atmosphere by a coating which does not allow penetration of water and electrolytes therethrough. An example of such a coating is lacquer. The second electrode structure is in fact not formed. a priori in the sensor but is formed when a water layer (including some electrolytes which are naturally present in the atmosphere) condenses or precipitates on the ex posed outer surface of the insulator (i.e. the surface which is not in contact with said first electrode). A measuring circuit is connected through wires to apply a current to both first and second electrode structures to detect a chance in capacitance between them.

According to said fifth embodiment it is preferable that the exposed outer surface of the insulator on which the second electrode. (being the water layer), is formed would be rough. in order to speed the dew condensation onset and to increase the sensitivity of the sensor. In addition said rough surface eliminates the salt contamination influence on the sensor's sensitivity. since only an essentially continuous water layer (not water drops alone which do not constitute a continuous layer) forms the second electrode structure.

The dew sensitivity of the sensor may be changed by varying the roughness of the insulator outer surface, on which the water condenses. For example, several detachable insulators with varying roughnesses may be used.

The dew sensitivity of the sensor may be also be changed by changing the infrared emission from the insulator outside surface. for example by changing the material. color or roughness of the surface.

The salt contamination influence may be eliminated by using a net (made either from conducting or insulating material) mounted on the outside surface of the insulator, which protects the insulator. The measuring circuit measures resistance between two or more leads connecting the circuit to the second and first electrodes, when the water layer forming the first electrode is present. The resistance is used as a gauge for the salt contamination of the sensor.

Printed circuit board. for example 0.5 mm thickness and 59×54 mm area may be used for the carrying out the sensor In the following, the present invention will be further described with reference to some non limiting drawings and examples.

BRIEF DESCRIPTION OF THE DRAWINGS

FIG. I shows a fiber-optical dew point hygrometer in accordance with a first option of the invention comprising a as blower as the restoring means.

DETAILED DESCRIPTION OF THE INVENTION

Figure 1:
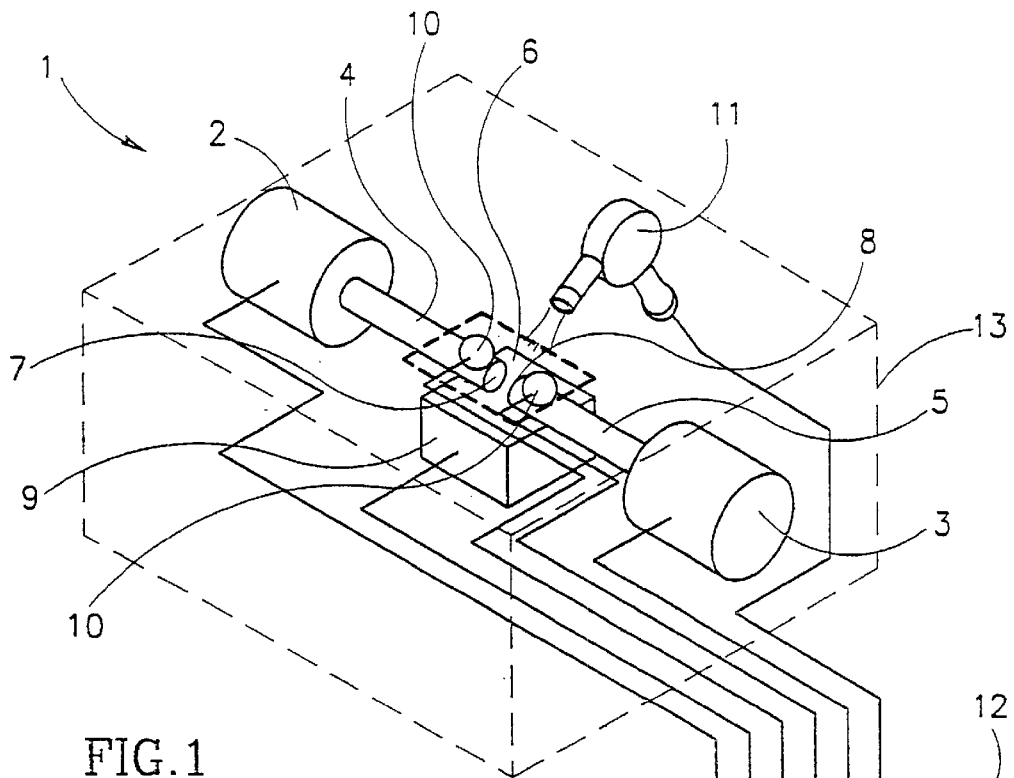

Reference is first made to FIG. I which shows a dew point hygrometer 1 in accordance with the first option of the first embodiment of the invention. The hygrometer comprises a light emitter 2 for example HFBR-1524 transmitter (Hewlett Packard Components. USA). a light detector 3 for example HFBR-2524 receiver (Hewlett Packard Components. USA). Light emitter 2 and light detector 3 are coupled through a light path defined by two optic fibers. a first optic fiber 4 coupled to the light emitter and a second optic fiber 5 coupled to the light detector. Optic fibers 4 and 5 are spaced from each other so as to form sensing gap 6 therebetween. The optic fibers are for Hewlett Packard plastic fiber optic cable HFBR-PUS001 diameter 1.0 mm (Hewlett Packard Components, USA). The uncoupled end of the first optic fiber 7 and the uncoupled end of the second optic fiber 8 serve as dew forming ends. These ends are in contact with the gas which dew point is to be determined. Formation of dew on ends 7 and 8 changes the light transmittance from light emitter 2 to light detector 3.

Dew forming ends lay on temperature control device 9. for example SP 1652 Harlow Industries Inc. (USA) thermo-electric cooler which device can control the temperature of dew forming ends 7 and 8 to a desired temperature. The hygrometer further comprises thermometers 10 which determines the temperature of dew forming ends 7 and 8. A gas blower 11 is positioned in the vicinity of dew forming ends 7 and 8 and can blow a gas stream strong enough to clear away liquid drops from dew forming ends 7 and 8.

The system comprises a control mechanism 12 which constantly receives input from light detector 3, and controls the operation of light emitter 2 temperature control device 9 and of gas blower 11.

Temperature control device 9 is under servo . control by control mechanism 12. Control mechanism 12 constantly controls the temperature of temperature control device 9 so that the input received from light detector 3 is essentially constant or in oscillations near the constant. As the dew contact of the gas rises temperature of control device 9 also rises in order to eliminate change of the light perceived by light detector 3. The changes in temperature displayed in the measurement process is used for dew point temperature calculations.

Periodically, for example every hour, the control mechanism 12 causes temperature control device 9 to substantially cool dew forming ends 7 and 8 so that a heavy coalescence. in the form of a water drop forms on dew forming ends, dissolving all solid deposits present thereon. Gas blower 11 is then activated and blows an air stream strong enough to clear away the water drop contain the dissolved deposits so that dew forming ends 7 and 8 are essentially restored to their original, contamination-free condition.

Hygrometer 1 is enclosed within a container 13. having an opening, so that only dew forming ends 7 and 8 are exposed to the Has while the remaining parts of the hygrometer are protected from contaminants.

Figure 2:
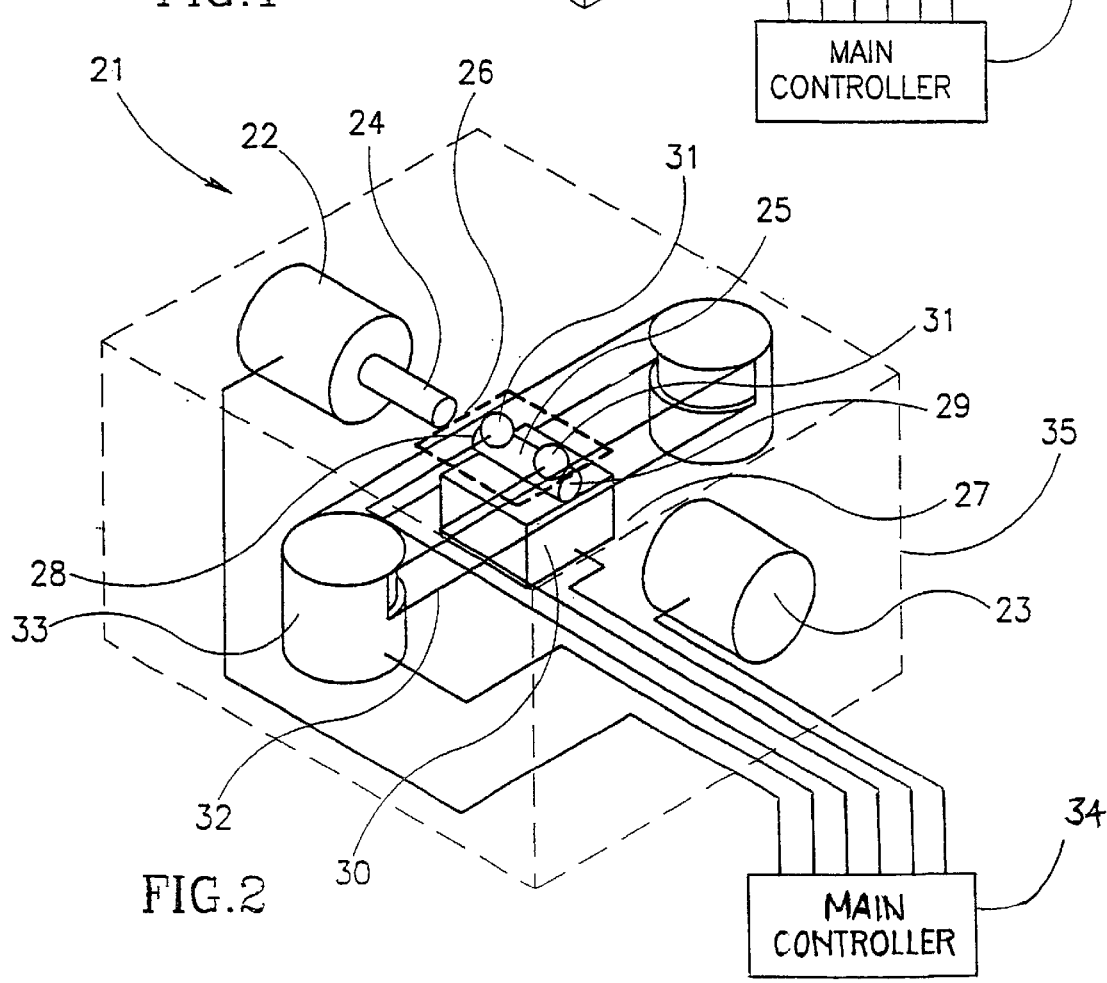
FIG. 2 shows a fiber-optical dew point hygrometer in accordance with a second option of the invention comprising a displaceable transparent film as the restoring means.

FIG. 2 shows a second option of the fiber-optical dew point hygrometer 21. The hygrometer comprises a light emitter 22, a light detector 23. a first optic fiber 24 coupled to the light emitter and a second optic fiber 25 spaced therefrom. The hygrometer comprises two sensing gaps, a first sensing gap 26 positioned between optic fibers 24 and 25 and a second sensing gap 27 between optic fiber 25 and light detector 23. Both ends of optic fiber 25, which are end 28 (forming sensing gap 26) and end 29 (forming sensing gap 27) serve as dew forming ends and lay on temperature control device 30 and their temperature is monitored by thermometers 31.

A transparent band 32, made for example of Polyester™ (Lee Filters, UK) is linearly displaceable over dew forming end 28 and 29. The band is displaced by movement of pulley block 33.

Control mechanism 34 is connected to the light emitter 22, light detector 23, temperature control means 30, thermometer 31 and the pulley block 33.

Dew forming essentially on the transparent band 32 present on dew forming end 28 and 29. Periodically, the control mechanism activates pulley block 33 so that band 32 is displaced and a new portion of the band. free of contamination is placed over the dew forming end. Protecting container 35 ensures that all parts of the hygrometer save for the dew forming ends of the portion of the band present thereon are protected from contamination.

Figure 3:
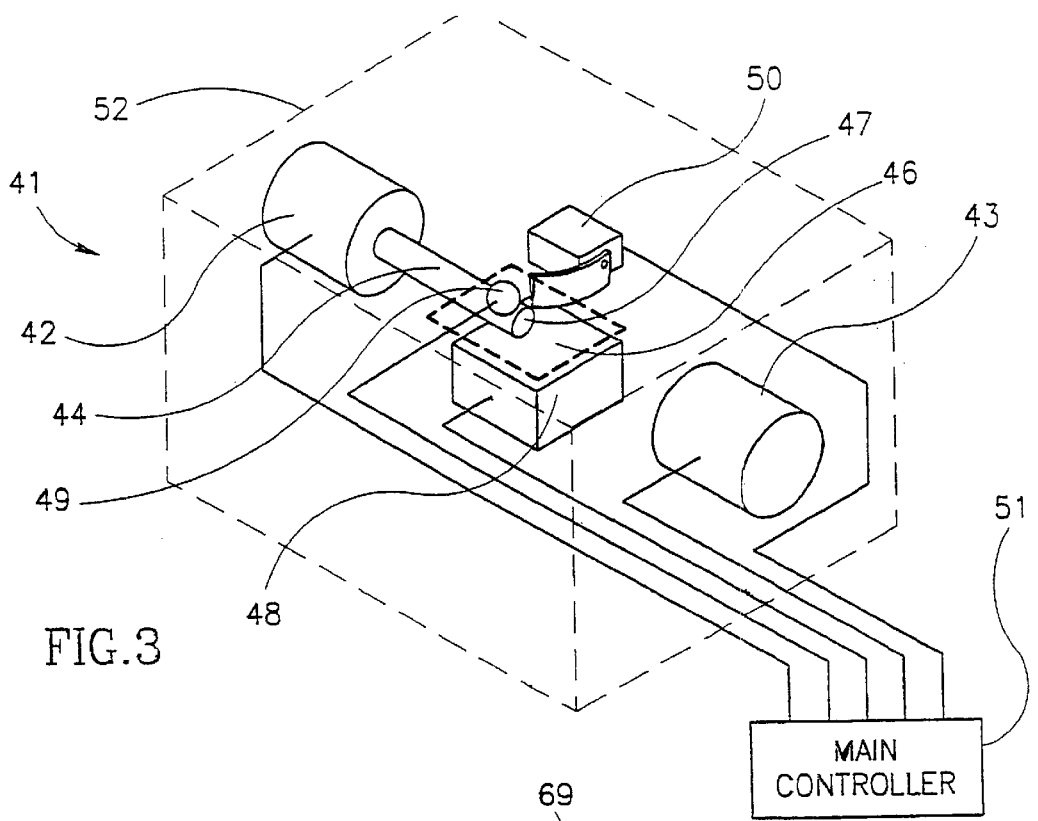
FIG. 3 shows a fiber-optical dew point hygrometer in accordance with a third option of the invention comprising a cutter as the restoring means.

FIG. 3 shows a fiber-optical dew point hygrometer 41 in accordance with the third option of the invention. The hygrometer comprises a light emitter 42. light detector 43 and a single optic fiber 44 coupled to the light emitter. The sensing gap 45 is formed between the uncoupled end of optic fiber 44 and the light detector. said uncoupled end 47 serves as the dew forming end and lays on temperature control device 48 and is in contact with thermometer 49. The hygrometer also comprises a movable cutter 50 capable of periodically slicing a very thin slice. for example several microns thick from the dew forming end 47 and thus eliminating a slice having solid deposits thereon and exposing a clean. contaminated-free end. After each slicing cutter 50 retraces exactly the distance it has eliminated so as to be in a position to cut another slice of the same size.

Control mechanism 51 is coupled to light emitter 42, light detector 43. temperature control mechanism 48 and cutter 50 and periodically activates the cutter so that a new contamination free dew forming end is periodically exposed. and protecting container 52 protects part of the hygrometer from contamination.

When calculation of the dew point is carried out the fact that the gap is progressively increased is taken into consideration when calculating the changes in light transmittance.

Figure 4:
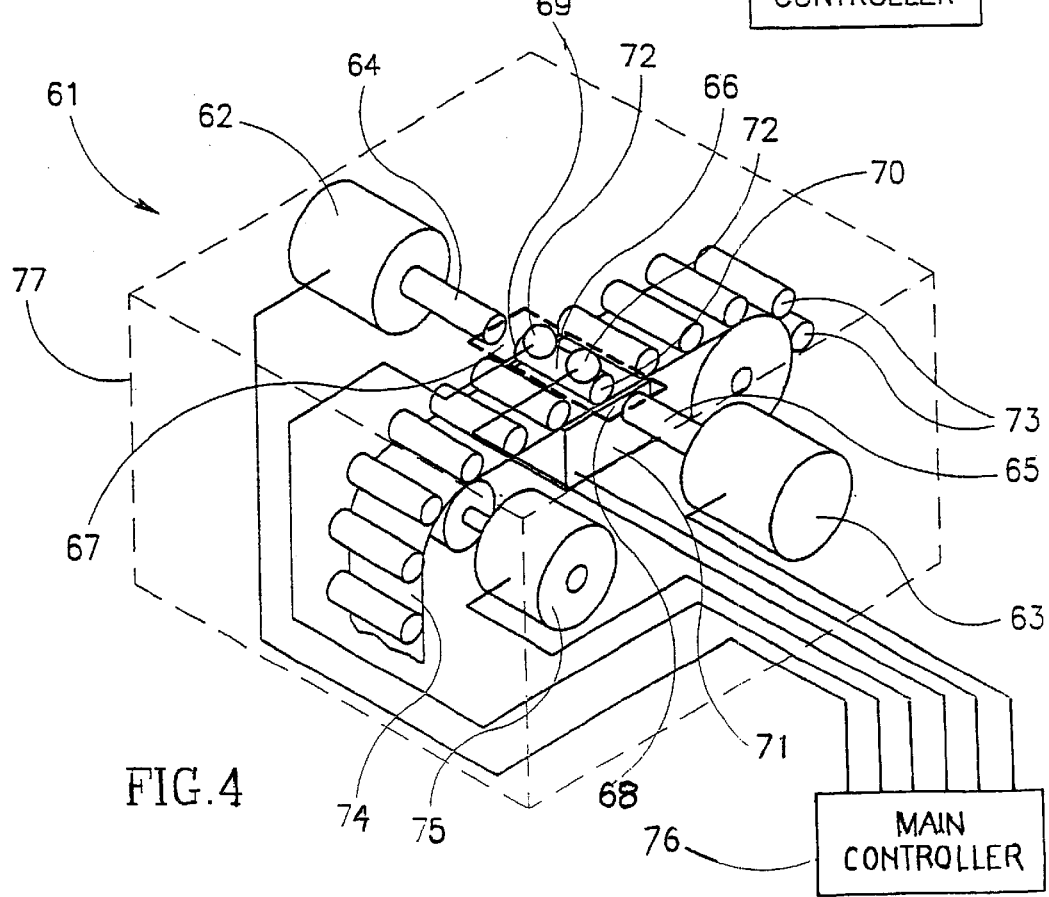
FIG. 4 shows a fiber-optical dew point hygrometer in accordance with a fourth option of the invention in which an intermediate optic fiber belongs to a battery of optic fibers and can be periodically replaced by another member in the battery.

FIG. 4 shows a fiber-optical dew point hygrometer 61 in accordance with the fourth option of the invention. The hygrometer comprises a light emitter 62 and light detector 63 and three optic fibers. A first peripheral optic fiber 64 coupled to the light emitter, a second peripheral optic fiber 65 coupled to the light detector and an intermediate optic fiber 66 positioned between the two peripheral optic fibers. Two sensing gaps are formed, a first sensing gap 67 between peripheral optic fiber 64 and the intermediate optic fiber 66 and a sensing gap 68 between intermediate optic fiber 66 and peripheral optic fiber 65. The ends of the intermediate optic fiber 69 and 70 serve as the dew forming ends and lay on temperature control device 71 and in contact with thermometers 72.

Intermediate optic fiber 66 is a member of a plurality of other. identical optic fibers 73. formed as a batten. for example on a conveyor belt 74 which identical optic fibers are advanced by movement of pulley, block 75. Control mechanism 75 is coupled to temperature control device 71. to light emitter 62. light detector 63 and to pullets block 75. Periodically control mechanism 76 activated pulley block 75 so that conveyor belt 74 is advanced and used optic fiber 66 having solid deposits thereon is replaced by contaminated-free optic fibers 73. Protecting container 77 ensures that the optic fibers 73 before usage are free from contamination.

Figure 5:
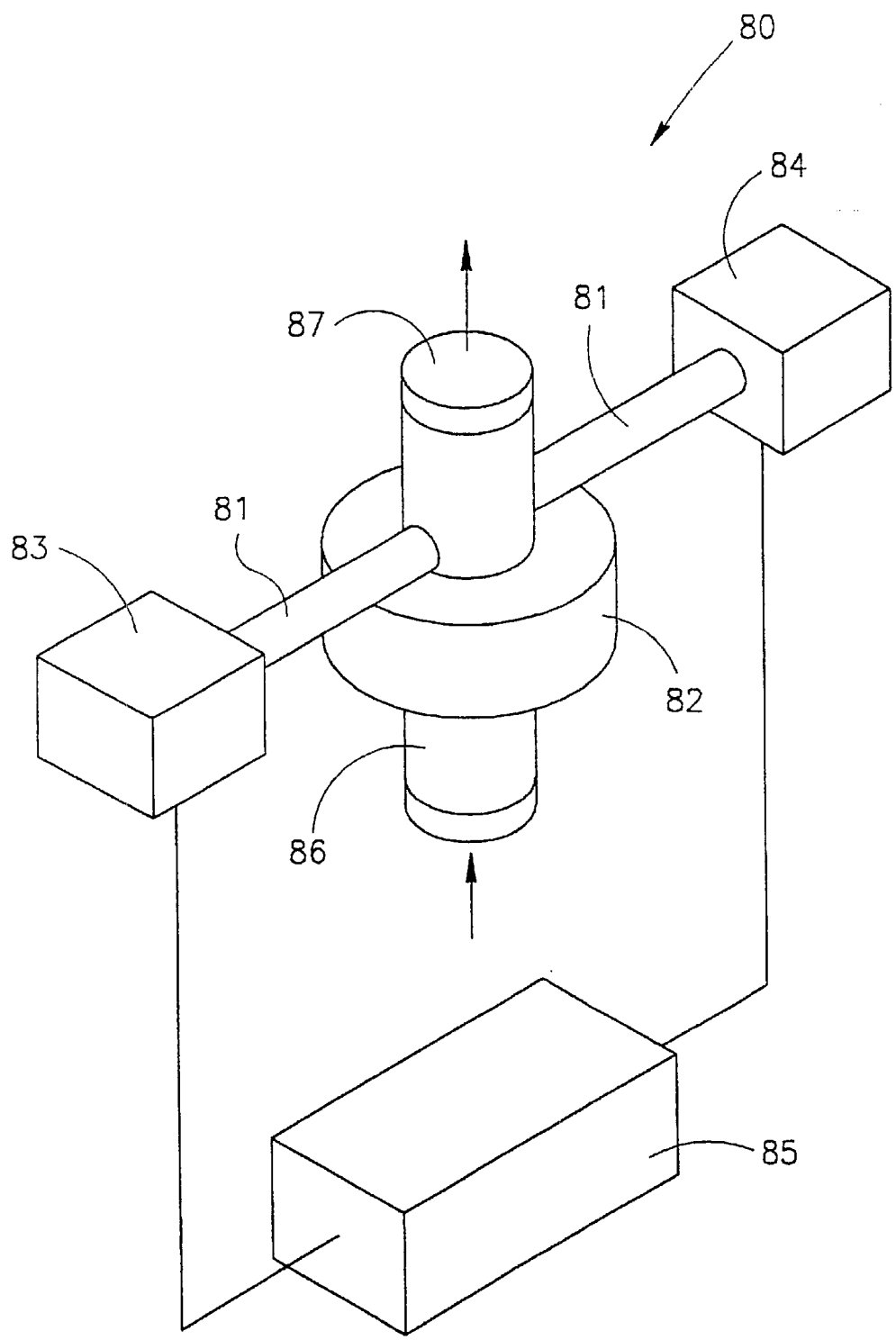
FIG. 5 shows a fiber-optical dew sensor in accordance with the second embodiment of the invention.

Reference is now made to FIG. 5 which shows a fiber-optical dew sensor in accordance with the second embodiment of the invention. for sensing the natural condensation. for example use in greenhouses. The dew sensor 80 comprises two optic fibers 81. having rough ends 88. The optic fibers have a gap therein-between 89. The optic fibers are embedded in a PVC white plate 82 which temperature is similar to the natural temperature of the ambient environment. One optic fiber 81 is connected to a light emitter 83, for example. HFBR-1524 transmitter (Hewlett Packard, Components, USA) and one optic fiber 81 is connected to a light detector 84. At night, while there is cooling. due to infrared emission of the plate 82 to the direction of the sky, the optic fibers 81 embedded in the plate are also cooled, and water condensates on the rough edges 88 of the optic fibers. filling the rough edges. and as a result the light transmitter in the optic system is increased.

An electronic control system 85 controls parameters of the light emitter 83 and light detector 84 and optionally, where the reading of humidity content is high, can give a warning to activate drying means in the greenhouse.

The light enters gap 89, through protector tube 86. which is fitted at both ends with filters 87. which filter out various contamination. and protects the ends of the fibers against dust and contamination.

According to experiments carried out with the above dew sensor. the temperature at night of the optic fiber placed in the white PVC plate. is smaller than the temperature of rose leafs only at 0.1–0.2° C. so that the plate actually mimics quite accurately the natural condition of the leaf. Where there is contamination of the ends of the fibers of a water soluble compound (such as sulfur) and the water condensates on the rough edges of the optic fibers. the compound becomes soluble in the water. and produces a solution which fills the rough ends. The transmittance of light through a solution is not much different than transmission of a light through clean water (not containing sulfur). Since the plastic material from which the optic fibers is made is resistant to corrosive and aggressive solutions, the dew sensors can still continue working even under quite extreme conditions typical of greenhouses.

Figure 6:
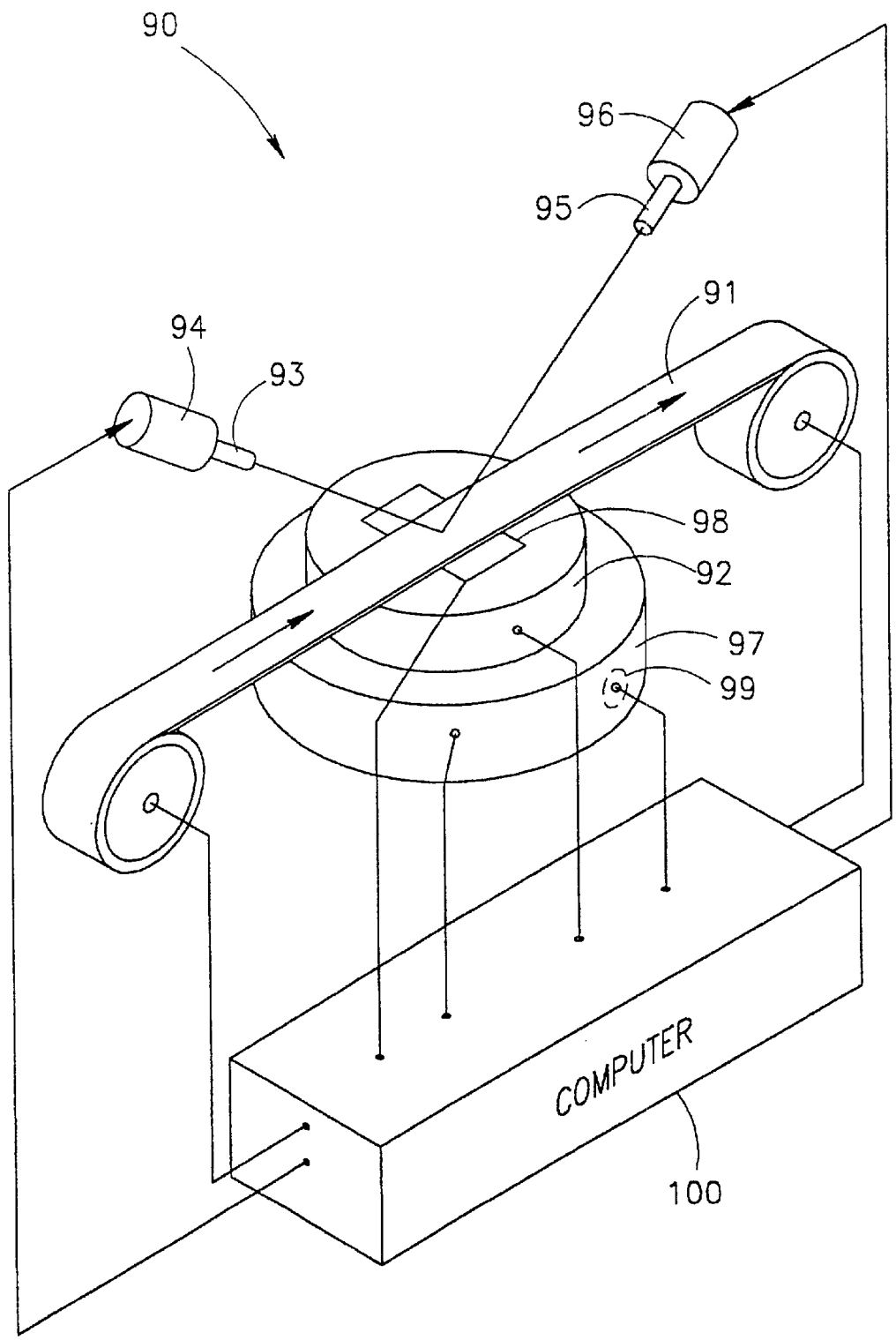
FIG. 6 shows a film dew point hygrometer or a dew sensor in accordance with the third embodiment of the invention.

Reference is now made to FIG. 6. which shows a film dew point hygrometer according to the third embodiment of the invention. comprising a condensation film. The dew point hygrometer 90 comprises a condensation film, for example a nylon transparent film 91 placed on a thermoelectric cooler 92. The film reflects light sent from light emitter 94. through optic fiber 93 into optic fiber 95 connected to light detector 96. With the use of a fan 97. air is mobilized on the condensation film, and cools the warm side of the thermometric cooler 92. While cooling condensation film 91, by thermoelectric cooler 92, water condensates on external side (i.e. the side facing upward) of the film and changes the light reflection from both sides of the film, which change is detected by light detector 96. Temperature sensors 98 and 99 measure the temperature of the condensation film and the air, respectively. An electronic control system 100 controls the work of the cooler 92. the light emitter 94 and the light detector 96. measures the temperature of the dew point (i.e. the temperature of the film in which dew forms thereon) and the air temperature obtained by sensors 98 and 99, and thus calculates the dew point of the measured air. A mobilizing system (not shown in the figure) advances each period of time. for example each week. film 91 which is present as a long continuous film, so that a new film is used every period for condensation and light reflector purposes. This ensures, that even if a specific portion of film is contaminated, distorting the reflection of light therefrom, a new film is used without said distortion. Of course new unused film is protected by contamination, for example by being placed in a protective container.

Figure 7:
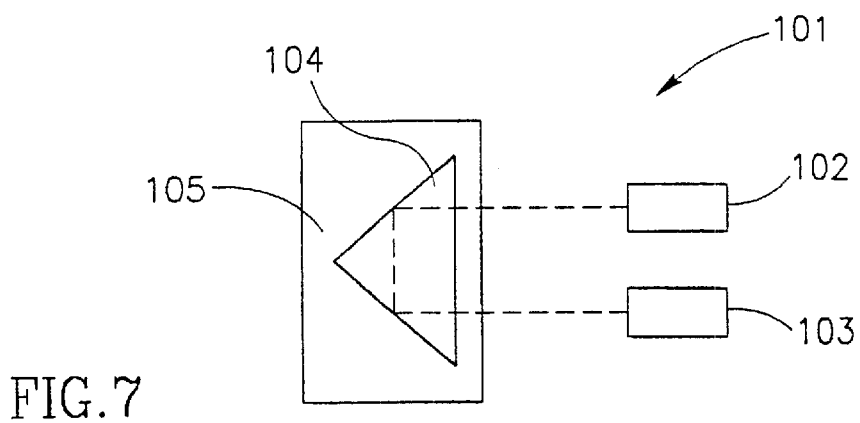
FIG. 7 shows a prism dew point hygrometer in accordance with the fourth embodiment of the invention.

FIG. 7 shows a prism dew point hygrometer 101 in accordance to the fourth embodiment of the invention. comprising an optical prism. The hygrometer comprises a light emitter 102. a light detector 103 and the prism 104 which is placed on a thermoelectric cooler 105. The prism reflects light sent from the light emitter to the light detector. While cooling the prism 104 by thermoelectric cooler 105. water condensates on the prism surfaces and changes the light reflection therefrom. Control mechanism (not shown) can control the temperature of the thermoelectric cooler to a temperature which causes condensation on the surfaces of the prism and as a result a change in the light detected.

Figure 8:
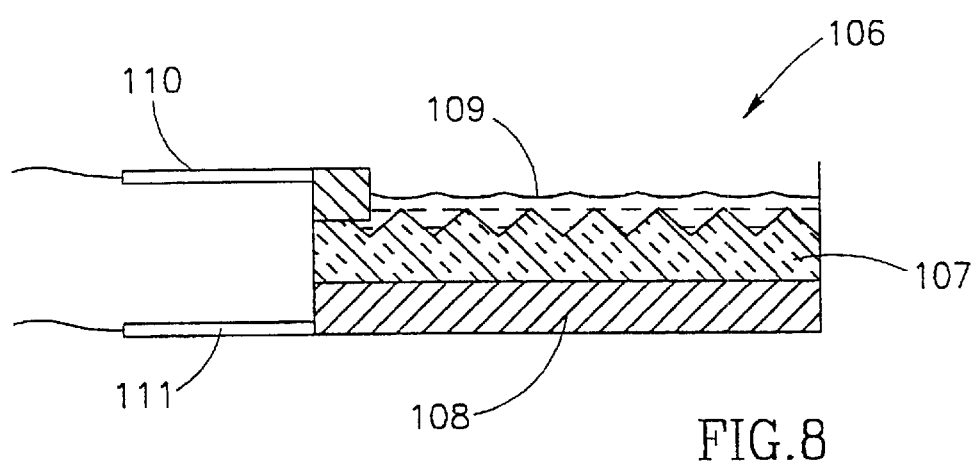
FIG. 8 shows a capacitive dew sensor in accordance with the fifth embodiment of the invention.

FIG. 8 shows a capacitive dew sensor 106 in accordance to the fifth embodiment of the invention. The sensor includes an insulator 107. a first electrode structure 108 isolated from the ambient atmosphere by a protective coat such as lacquer which protective coat does not allow penetration of humidity and electrolytes therethrough. The sensor comprises a second electrode structure 109 formed by water layer which condensates on the exposed outer surface of the insulator 107. The waters are conductive due to the fact that they contain naturally appearing salts present in the air. The sensor is connected to the measuring circuit (not shown) by wires 110 and 111. When water is present as shown in FIG. 8. electrode 109 is formed. and as a result the capacitance changes somewhat from 0.1 to 160 picofarads and said change in capacitance can be measured. By another option. it is possible to add a net covering outside surfaces of insulator 107 in order to decrease the effect of air-born salts on the sensitivity of the sensor.

Figure 9:
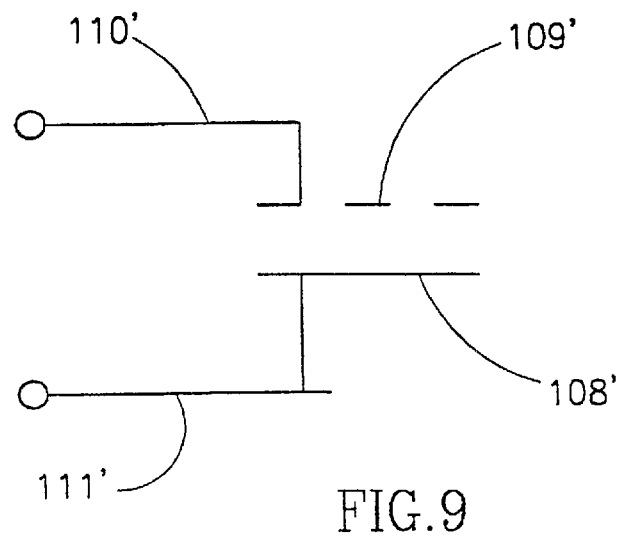
FIG. 9 shows a schematic representation of the electric circuit of FIG. 8.

FIG. 9 illustrates the schematic equivalent circuit of the capasitive sensor created by the first electrode structure 108' with constant area and the second electrode structure 109'. created by water layer. with variable area where 110' and 111' are the wires connecting to the measuring circuit (not shown).

What is claimed is:

1. A capacitive dew sensor comprising:

a first electrode separated from the ambient environment by a coating which does not allow pentagon of humidity and electrolyte therethrough; an insulator mounted on said first electrode, a second electrode formed on the exposed outer surface of the insulator when water containing electrolytes condenses or precipitates on said exposed outer surface of the insulator to form a continuous layer;

electric wires connecting the two electrode structures to a measuring circuit for applying a current to said first and second electrode structures, so as to detect a change in capacitance between said first and second electrode structures when water layer is present.

2. The capacitive dew sensor according to claim 1, wherein the exposed outer surface of the insulator o which water condensates to form the second electrode structure is rough.

3. The capacitive dew sensor according to claim 1, wherein an absorbent material is mounted on the exposed outer surface of the insulator, thereby speeding the dew condensation onset and to increase the sensitivity of the sensor.

4. The capacitive dew sensor according to claim 3, further comprising a net mounted on the outer surface of the insulator.

* * * * *